United States Patent [19]

Fleming et al.

[11] Patent Number: 4,874,871
[45] Date of Patent: Oct. 17, 1989

[54] PROCESS FOR PREPARING (+)-2,3-DIHYDRO-1H-PYRROLO[1,2-A]PYRROLE-1-CARBOXYLIC ACID AND RELATED COMPOUNDS

[75] Inventors: Michael P. Fleming, Longmont; George C. Schloemer, Lyons; Hiralal N. Khatri, Louisville, all of Colo.

[73] Assignee: Syntex (U.S.A.) Inc., Palo Alto, Calif.

[21] Appl. No.: 30,774

[22] Filed: Mar. 25, 1987

[51] Int. Cl.$^4$ ............... C07D 487/04; C07D 207/337; C07D 207/333
[52] U.S. Cl. .................... 548/543; 548/561; 548/562
[58] Field of Search .............. 548/543, 561, 562; 546/112, 138

[56] References Cited

U.S. PATENT DOCUMENTS

| | | | |
|---|---|---|---|
| 4,072,498 | 2/1978 | Moon et al. | 71/92 |
| 4,087,539 | 5/1978 | Muchowski et al. | 424/274 |
| 4,089,969 | 5/1978 | Muchowski et al. | 424/274 |
| 4,097,579 | 6/1978 | Muchowski et al. | 424/274 |
| 4,140,698 | 2/1979 | Van Horn et al. | 260/326.55 M |
| 4,344,943 | 8/1982 | Muchowski | 424/245 |
| 4,347,186 | 8/1982 | Muchowski et al. | 548/516 |
| 4,353,829 | 10/1982 | Thurber et al. | 260/326.25 |
| 4,496,741 | 1/1985 | Doherty | 548/453 |
| 4,511,724 | 4/1985 | Chang et al. | 548/452 |
| 4,533,671 | 8/1985 | Biftu et al. | 514/413 |
| 4,536,512 | 8/1985 | Biftu et al. | 514/413 |

FOREIGN PATENT DOCUMENTS

| | | |
|---|---|---|
| 41711 | 12/1981 | European Pat. Off. . |
| 53021 | 6/1982 | European Pat. Off. . |
| 0091181 | 10/1983 | European Pat. Off. . |
| 804567 | 4/1951 | Fed. Rep. of Germany . |
| 49-16870 | 4/1974 | Japan ................ 548/550 |
| 0126887 | 1/1960 | U.S.S.R. .............. 548/543 |
| 1234139 | 6/1971 | United Kingdom . |

OTHER PUBLICATIONS

Pizzorno et al., J. Org. Chem., 39(5), 731 (1974).
Carpio et al., Can. J. Chem., 60, 2295–2312 (1982).
Synth. Commun., 1984, 14(5), 453–464, Muchowski et al. and C.A. 101(19), 171016t.
Can. J. Chem. 1983, 61(3), 454–456, Galeazzi et al. and C.A. 98 (25), 215437g.

*Primary Examiner*—David B. Springer
*Attorney, Agent, or Firm*—Derek P. Freyberg

[57] ABSTRACT

2,3-Dihydro-1H-pyrrolo[1,2-a]pyrrole-1-carboxylic acid compounds of the formula,

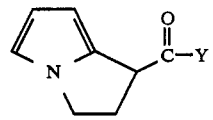

in which Y is
  OH;
  O$^-$M$^+$, wherein M is an alkali metal; or
  NRR', wherein R is lower alkyl and R' is lower alkyl or aryl, or NRR' is the residue of a saturated cyclic amine, are prepared from pyrrole.

20 Claims, No Drawings

PROCESS FOR PREPARING (+)-2,3-DIHYDRO-1H-PYRROLO[1,2-A]PYRROLE-1-CARBOXYLIC ACID AND RELATED COMPOUNDS

BACKGROUND OF THE INVENTION

1. Field of the Invention

This invention relates to pyrrolo[1,2-a]pyrroles, and especially to the synthesis of (±)-2,3-dihydro-1H-pyrrolo[1,2-a]pyrrole-1-carboxylic acid and related compounds.

2. Background of the Invention

5-Aroyl-2,3-dihydro-1H-pyrrolo[1,2-a]pyrrole-1-carboxylic acids, also known as 5-aroyl-2,3-dihydro-1H-pyrrolizine-1-carboxylic acids, of formula I, and the

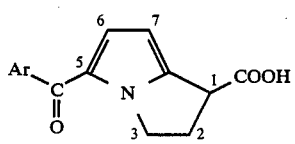

(I)

pharmacologically acceptable salts and esters thereof, are useful as analgesic, anti-inflammatory, and antipyretic agents for mammals, including man. They are also smooth muscle relaxants. Two exemplary compounds under clinical study in man are ketorolac, 5-benzoyl-2,3-dihydro-1H-pyrrolo[1,2-a]pyrrole-1-carboxylic acid, (I, Ar=$C_6H_5$), and anirolac, 5-p-anisoyl-2,3-dihydro-1H-pyrrolo[1,2-a]pyrrole-1-carboxylic acid, (I, Ar=p-$CH_3O$-$C_6H_5$), both disclosed in U.S. Pat. No. 4.089,969 to Muchowski et al. Other compounds, where the 5-aroyl substituents are substituted or unsubstituted benzoyl, furoyl, thenoyl, and pyrroyl, and where the 6-position on the pyrrolo-pyrrole nucleus is optionally substituted by lower alkyl or halogen, and the uses thereof, are also disclosed in a series of patents assigned to Syntex (U.S.A.) Inc., beginning with U.S. Pat. No. 4,089,969, and including U.S. Pat. Nos. 4,087,539; 4,097,579; 4,140,698; 4,232,038; 4,344,943; 4,347,186; 4,458,081; 4,347,187; 4,454,326; 4,347,185; 4,505,927; 4,456,759; 4,353,829; 4,397,862; 4,457,941; and 4,454,151. U.S. Pat. Nos. 4,511,724 and 4,536,512, assigned to Merck & Co., Inc., disclose 5-(substituted pyrrol-2-oyl)-2,3-dihydro-1H-pyrrolo[1,2-a]pyrrole-1-carboxylic acid derivatives and 5-(2,3-dihydro-1H-pyrrolo[1,2-a]pyrrol-2-oyl)-2,3-dihydro-1H-pyrrolo[1,2-a]pyrrole-1-carboxylic acid derivatives, respectively; while U.S. Pat. No. 4,533,671, also assigned to Merck & Co., Inc., discloses 5-(2,3-dihydro-1H-pyrrolo[1,2-a]pyrrol-2-oyl)-2-pyrrolealkanoic acids and analogs.

Various methods for the preparation of these pyrrolopyrroles are exemplified in the patent and chemical literature, and many proceed through a common intermediate, 2,3-dihydro-1H-pyrrolo[1,2-a]pyrrole-1-carboxylic acid, (II), or its alkyl ester;

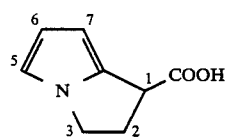

(II)

The alkyl ester may be readily 5-aroylated by methods such as those described in the previously-cited patents and in U.S. Pat. No. 4,496,741 to Doherty, and saponified, to yield a 5-aroyl-2,3-dihydro-1H-pyrrolo[1,2-a]pyrrole-1-carboxylic acid (I).

Several methods of preparation of compound (II) are known in the patent and chemical literature, with most proceeding through 2,3-dihydro-1H-pyrrolo[1,2-a]pyrrole-1,7-dicarboxylic acid, which is selectively decarboxylated, by methods also described in the literature, to the 1-carboxylic acid.

Syntheses not involving the 1,7-dicarboxylate include those set forth in, for example, U.S. Pat. Nos. 4,140,698 and 4,344,943, referred to previously. These syntheses involve the preparation of 1-(2-iodoethyl)-pyrrole-2-acetonitrile (III, Z=CN) or an alkyl 1-(2-iodoethyl)-pyrrole-2-acetate (III, Z=COOR) and coupling to form the saturated ring, giving compound (IV).

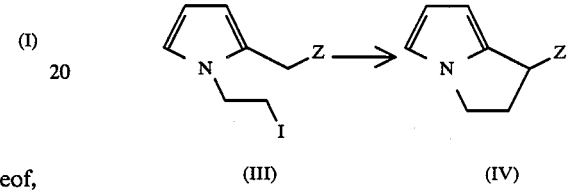

U.S. Pat. No. 4,347,186 discloses a synthesis of (I) by the cyclization of a 1-[3,3-di(alkoxycarbonyl)-propyl]-2-methanesulfonyl-5-aroylpyrrole (V) to the 1,1-dicarboxylate (VI), followed by hydrolysis to the 1-carboxylate.

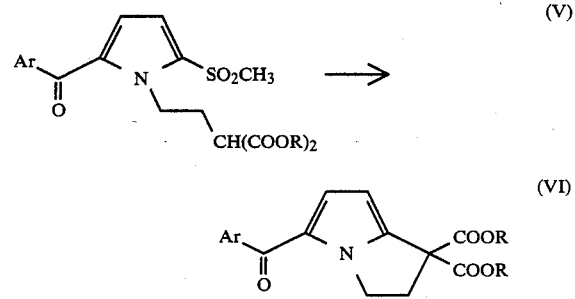

Commonly assigned U.S. patent application Ser. No. 06/868,835, filed May 19, 1986, discloses a similar synthesis in which a 1-[3,3-di(alkoxycarbonyl)propyl]-2-halo-5-aroylpyrrole is converted to the 1,1-dicarboxylate (VI), followed by hydrolysis to the 1-carboxylate.

In each of these patents, the saturated ring is formed wholly or partially by the N-substituent on the pyrrole.

Pizzorno et al., in J. Org. Chem., v.39, p.731 (1974), disclose the cycloaddition of ethyl propiolate to N-formyl-L-proline (VII) to yield ethyl 2,3-dihydro-1H-pyrrolo[1,2-a]pyrroly-7-carboxylate (VIII), which is subsequently reduced to the corresponding pyrrolizidine carboxylate.

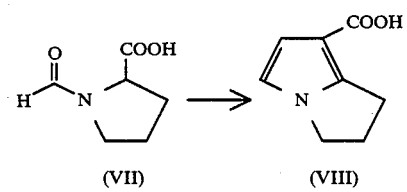

British Pat. No. 1,234,139 discloses compounds including 7-hydroxymethyl- and 7-formyl-2,3-dihydro- 1H-pyrrolo[1,2-a]pyrrole, prepared from the alkaloid derivative supinidine.

The disclosures of these patents and articles, and other patents and articles referred to throughout this specification, are incorporated herein by reference.

SUMMARY OF THE INVENTION

In a first aspect, this invention relates to the preparation of (±)-2,3-dihydro-1H-pyrrolo[1,2-a]pyrrole-1-carboxylic acid compounds of formula IX,

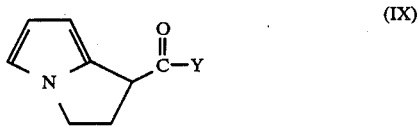

(IX)

in which Y is
OH;
O⁻M⁺, wherein M is an alkali metal; or
NRR', wherein R is lower alkyl and R' is lower alkyl or aryl, or NRR' is the residue of a saturated cyclic amine,
from pyrrole.

The preparation may be represented schematically:

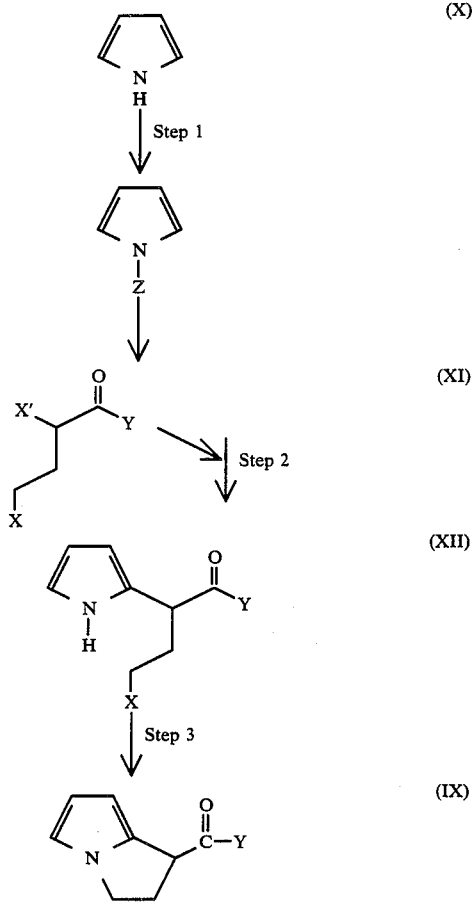

in which
Y is as previously defined;
X and X' are independently halogen; and
Z is Li, MgCl, or MgBr.

In a second aspect, this invention relates to a process for preparing (±)-2,3-dihydro-1H-pyrrolo[1,2-a]-pyrrole-1-carboxylic acid (IX, Y=OH), which comprises preparing a compound of formula IX, where Y is other than OH, by the process described above, followed by hydrolysis thereof, or preparing an ester thereof (IX, Y=OR) by preparing the acid (IX, Y=OH), followed by esterification.

In a third aspect, this invention relates to novel compounds of formula XII which are useful as intermediates in the process herein.

DETAILED DESCRIPTION OF THE INVENTION

Definitions

Unless otherwise stated, the following terms used in the specification and claims have the meanings given below:

"lower alkyl", denoted generally by R or R', refers to straight, branched, or cyclic saturated hydrocarbon radicals having from one to six carbon atoms, e.g. methyl, ethyl, isopropyl, cyclopropylmethyl, pentyl, cyclohexyl, and the like. Preferred lower alkyls are methyl, ethyl, and n-propyl, and a particularly preferred lower alkyl is methyl. If more than one alkyl radical is present in a given molecule, each may be independently selected from "lower alkyl" unless otherwise stated.

"lower alkoxide", "lower alkanol", "lower alkylamine", "lower alkyl ester", and similar terms refer to alkoxides, alkanols, alkylamines, alkyl esters, etc. in which the (or each) alkyl radical is a "lower alkyl" as defined above.

"aryl", denoted generally by R', includes phenyl, phenyl substituted by one to three lower alkyl, lower alkoxy, or halogen radicals (e.g. 4-tolyl, 4-fluorophenyl, etc.), and the like.

"halogen", denoted generally by X or X', refers to chlorine, bromine, or iodine. Preferred halogens are chlorine and bromine.

"aprotic polar solvent" includes organic solvents which may be either water-immiscible, such as halogenated hydrocarbons, e.g. methylene chloride, chloroform, etc., or water-miscible, such as tetrahydrofuran, dimethoxyethane, bis(2-methoxyethyl) ether (diglyme), dimethylformamide, N-methylpyrrolidone, dimethylsulfoxide, etc. The solvent may also contain minor proportions of aprotic non-polar solvents such as hydrocarbons, e.g. cyclohexane, toluene, and the like, provided that the solvent properties are largely determined by the polar solvent.

"residue of a saturated cyclic amine" refers to the residue (i.e. that part other than the N-bonded hydrogen atom) of a saturated cyclic amine containing 5 or 6 ring atoms, e.g. pyrrolidine, piperidine, piperazine, morpholine, and the like.

"strong base" refers to bases such as alkali metal hydroxides, lower alkoxides, hydrides, di(lower alkyl)amines, and the like, e.g. sodium hydroxide, potassium methoxide, sodium hydride, lithium di(isopropyl)amine, lithium bis(trimethylsilyl)amine, etc.

Starting Materials and Purification

The starting pyrrole and compounds of formula XI, the products of formula IX, and the intermediates of formulae X and XII, may be isolated and purified, if desired, using conventional techniques, including but not limited ot filtration, distillation, crystallization, chromatography, and the like. They may be characterized using conventional means, including physical constants and spectral characteristics.

Preparation of Compounds of Formula XI

The 2-X'-4-X-butanoic acid derivatives of formula XI may be prepared by methods known to the art. See, for example, West German Pat. No. 804 567 (BASF), which is incorporated herein by reference, for the preparation of 2-bromo-4-chloro- and 2,4-dichlorobutanoyl chloride. Other acid halides may be prepared in a similar manner, and the acid halides may be converted to the desired amides or acid salts by methods known to the art, e.g., reaction with a diamine or hydrolysis.

Preparation of Compounds of Formula IX

In Step 1, the pyrrole is lithiated or converted to a Grignard reagent by methods well known to the art. For example, 1-lithiopyrrole is readily prepared by the reaction of pyrrole, typically in solution in an aprotic solvent such as a di(lower alkyl) ether, tetrahydrofuran, and the like, with an alkyllithium, e.g. n-butyllithium in hexane or similar solution, at a temperature between about 0 and 50° C., generally at reduced temperatures, e.g., near 0° C. 1-pyrrolemagnesium chloride (or bromide) is readily prepared by the reaction of pyrrole, again typically in solution in an aprotic solvent, which an alkylmagnesium chloride (or bromide), typically also in solution in an aprotic solvent, e.g. methylmagnesium chloride in THF, generally at reduced temperatures. The reactions are generally performed under an inert atmosphere, e.g. nitrogen, and occur rapidly, typically within 10 minutes. The resulting 1-lithiopyrrole or 1-pyrrolemagnesium chloride/bromide solutions are generally used immediately in Step 2.

In Step 2, the 2-X'-4-X-butanoic acid derivative of formula XI is treated with the pyrrole reagent (X) from Step 1 until reaction is complete. The pyrrole reagent (X) is preferably present in excess, for example between 1.2-fold and 3-fold excess, typically about a 2-fold excess, over compound (XI) to minimize the formation of 2,5-disubstituted pyrrole products. The reaction is generally performed under an inert atmosphere, by addition of a solution of compound (XI) in an aprotic polar solvent to a stirred solution of the pyrrole reagent (X), e.g the solution from Step 1. The reaction temperature may be from about 0 to 60° C., but the reaction is slowed by cooling, and addition typically takes place at reduced temperatures, e.g. near 0%C, in one or more portions; after which the reaction mixture is allowed to warm to up to 40° C., preferably room temperature (15°-25° C.), allowing the reaction to proceed to completion. The reaction time may range from 30 minutes to 48 hours, but is ordinarily 5-20 hours. Following completion of the reaction (the progress of which may be checked by methods such as thin layer chromatography, etc.), the resulting intermediates of formula XII may be isolated by conventional techniques, such as addition of water and acidification of the solution with mineral acid, e.g. by addition of concentrated hydrochloric acid to pH 1, followed by extraction into a suitable organic solvent, e.g. ether, and evaporation of the solvent. They may be purified most readily by chromatography.

Cyclization to the pyrrolo[1,2-a]pyrrole derivative for formula IX takes place in Step 3. Here, the intermediate of formula XII is dissolved in an aprotic polar solvent, e.g. THF, and treated with an excess of a strong base such as an alkali metal hydride, preferably sodium hydride. The reaction takes place typically at room temperature (15°-25° C.), in about 10 minutes to 10 hours, preferably in 1-5 hours, under an insert atmosphere. The excess hydride is destroyed, e.g. by slow addition of water, and the product of formula IX may then be recovered, e.g. for the amide by addition of a suitable organic solvent, such as ether, washing, and removal of the solvent; for the acid, by acidification, extraction of the acid into an organic phase, and evaporation of the solvent.

Conversion to the Acid/Ester of Formula IX

The amide of formula IX, where Y is NRR', may be converted into the acid by either acid- or base-catalyzed hydrolysis. For example, the amide may be treated with a dilute solution of a strong mineral acid, such as sulfuric acid, generally at elevated temperatures, e.g. up to reflux temperature, until hydrolysis is complete, and the resulting acid (IX, Y=OH) recovered in the manner described above. Alternatively, the amide may be treated with a solution of a strong base, such as an alkali metal hydroxide, typically in a protic organic solvent, generally at elevated temperatures, until hydrolysis is complete; water added and the resulting solution acidified; and the resulting acid (IX, Y=OH) separated, e.g. by extraction into an immiscible organic solvent. The acid of formula IX, obtained either in Step 3 or by the conversion just described, may be converted to a desired ester by conventional esterification techniques, e.g. reaction with an alcohol in the presence of an acid catalyst.

Preparation of Compounds of Formula I

Esters of compound (II, Y=OR) may be converted into the corresponding 5-aroyl-2,3-dihydro-1H-pyrrolo[1,2-a]pyrrole-1-carboxylic acids by 5-aroylation, followed by hydrolysis. The 5-aroylation may be performed by methods known to the art, e.g. Vilsmeier-Haack or Friedel-Crafts aroylations, and described in the patents cited in the "Background to the Invention" section of this application, especially U.S. Pat. Nos. 4,089,969 and 4,347,186 (using dialkylamides) and U.S. Pat. No. 4,353,829 (using morpholides), and the hydrolysis may be performed as described above.

Novel Intermediates

The compounds of formula XII are novel, and are useful as intermediates in preparing compounds of formula I, which are therapeutically useful as discussed above.

EXAMPLES

The invention is further illustrated, without limitation, by the following examples.

Example 1

Preparation of 2-bromo-4-chlorobutanoyl chloride.

A. 2-Bromo-γ-butyrolactone was treated according to the procedure of West German Pat. No. 804 567, to produce 2-bromo-4-chlorobutanoyl chloride. Thus, 2-bromo-γ-butyrolactone (Aldrich, 99.51 g, 603 mmol) and zinc(II) chloride (Alfa ultrapure, 8.45 g, 62 mmol) were added to a 250 mL three-neck flask containing a stirring bar and fitted with an addition funnel and a reflux condenser. The mixture was heated to 65° C. with stirring, and thionyl chloride (82.43 g, 693 mmol) was added through the addition funnel over 1 hour. Since a sample taken after 16 hours showed substantial remaining lactone, the mixture was cooled briefly, additional zinc(II) chloride (5.43 g, 40 mmol) was added, and the mixture heated for an additional 44 hours at about 65° C. Dichloromethane (100 mL) was then added, the resulting solution rapidly filtered through a coarse glass frit, and the thionyl chloride and dichloromethane removed by evaporation under aspirator vacuum at about 30° C. Distillation of the residue through a short packed column gave 87.51 g (66% yield) of a yellow oil, having a boiling point under aspirator vacuum of 108°–110° C. An NMR spectrum was consistent with 2-bromo-4-chlorobutanoyl chloride.

B. Substituting 2-chloro-γ-butyrolactone for 2-bromo-γ-butyrolactone, and using a similar procedure to that in part A of this Example, one obtains
2,4-dichlorobutanoyl chloride.

C. Similarly, substituting thionyl bromide for thionyl chloride and zinc(II) bromide for zinc(II) chloride in the procedure of parts A and B of this Example, one obtains
2,4-dibromobutanoyl bromide, and
2-chloro-4-bromobutanoyl bromide.

Example 2

Preparation of
N,N-diethyl-2-bromo-4-chlorobutanamide.

A. 2-Bromo-4-chlorobutanoyl chloride (101.7 g, 463 mmol) was added to a 1 L three-neck flask fitted with mechanical stirrer, addition funnel, and thermometer, and the flask then purged with nitrogen. Dichloromethane (400 mL0 was added, and the flask cooled in an ice bath to 0° C. Diethylamine (Baker, 66.8 g, 913.5 mmol) was added dropwise over 75 minutes, with the temperature rising to 5°–10° C., after which the ice bath was removed and the flask warmed to room temperature (about 20° C.) with a warm water bath, and the reaction mixture stirred for 30 minutes at that temperature. Water (250 mL) was added to the mixture; and the organic phase was separated, washed with water (2×250 mL), aqueous $KHCO_3$ (2×100 mL), and brine (100 mL), and dried over anhydrous magnesium sulfate. Removal of the solvent at 50° C. under reduced pressure gave a brown oil, which was distilled (Kugelrohr, 95° C., 0.15 mm) to afford 108.5 g (92% yield) of an extremely pale green oil, having an NMR spectrum consistent with N,N-diethyl-2-bromo-4-chlorobutanamide.

B. Substituting for 2-bromo-4-chlorobutanoyl chloride, in the procedure of part A of this Example,
2,4-dichlorobutanoyl chloride,
2,4-dibromobutanoyl bromide, or
2-chloro-4-bromobutanoyl bromide,
one obtains, respectively,
N,N-diethyl-2,4-dichlorobutanamide.
N,N-diethyl-2,4-dibromobutanamide.
N,N-diethyl-2-chloro-4-bromobutanamide.

C. Similarly, substituting other di(lower alkyl)amines, aryl(lower alkyl)amines, or cyclic amines for diethylamine, one obtains N,N-di(lower alkyl)- or N-aryl-N-(lower alkyl)-2-halo-4-halobutanamides, 2-halo-4-halobutanoylmorpholides, and the like.

Example 3

Preparation of the pyrrole reagent. (Step 1)

A. Pyrrole (Eastman, distilled over $CaH_2$, 0.60 g, 8.95 mmol) and tetrahydrofuran (distilled over sodium, 20 mL) were added to a 100 mL flask containing a stirrer bar, under strictly anhydrous conditions, and the flask cooled in an ice bath. n-Butyllithium (Aldrich, 2.6 M in hexane, 3.0 mL, 7.80 mmol) was added via syringe over about 1 minute, and the clear solution was stirred for 5 minutes. The resulting solution of 1-lithiopyrrole was used in Step 2.

B. Pyrrole (Eastman, distilled over $CaH_2$, 1.49 g, 22.2 mmol) and tetrahydrofuran (distilled over sodium, 30 mL) were added to a 100 mL flask containing a stirrer bar, under strictly anhydrous conditions, and the flask cooled in an ice bath. Methylmagnesium chloride (3.0 M in THF, 7.2 mL, 21.6 mmol) was added via syringe over about 5 minutes, during which time the temperature rose to about 20° C., and the mixture was stirred for 15 minutes. The resulting white slurry containing 1-pyrrolemagnesium chloride was used in Step 2.

C. Substituting methylmagnesium bromide for methylmagnesium chloride in the procedure of part B of this Example, one obtains
1-pyrrolemagnesium bromide.

Example 4

Preparation of α-(2-chloroethyl)-N,N-diethyl-1H-pyrrole-2-acetamide. (Step 2)

A. To the solution of 1-lithiopyrrole from part A of Example 3, maintained at 0° C. in the ice bath, was added N,N-diethyl-2-bromo-4-chlorobutanamide (1.09 g, 4.25 mmol) in a single portion via syringe. Within 30 minutes of stirring at 0° C., the initially yellow solution had become dark purple; and stirring at 0° C. was continued for 2 hours. The solution was then allowed to warm to room temperature, and stirred for 17 hours. Water (10 mL) was then added, and the mixture acidified to pH 1 with concentrated HCl, then diluted with ether (150 mL). washed with water (2×20 mL), aqueous $KHCO_3$ (2 x 20 mL), and brine (20 mL), and stirred over $MgSO_4$ and Filtrol. Rotary evaporation of the solvents under reduced pressure gave 0.72 g of a brown oil, which was shown by NMR spectra and thin-layer chromatography to contain a major proportion of α-(2-chloroethyl)-N,N-diethyl-1H-pyrrole-2-acetamide, (XII, X=Cl, Y=NEt₂), a minor proportion of N,N-diethyl-2,3-dihydro-1H-pyrrolo[1,2-a]pyrrole-1-carboxamide (IX, Y=NEt₂), and very minor proportions of the pyrrole-2,5-di(substituted acetamide) and unreacted N,N-diethyl-2-bromo-4-chlorobutanamide.

B. To the slurry containing 1-pyrrolemagnesium chloride from part B of Example 3, maintained at 0° C. in the ice bath, was added N,N-diethyl-2-bromo-4-chlorobutanamide (2.77 g, 10.8 mmol) in 15 mL Na-distilled tetrahydrofuran over 2.75 hours via syringe pump. The reaction mixture was stirred for 30 minutes at 0° C., then allowed to warm to room temperature, and stirred for 19 hours, resulting in a brownish-black solution. Water (10 mL) was then added, and the mixture acidified to pH 1 with concentrated HCl, then diluted with ether (150 mL), washed with water (2×25 mL), aqueous $KHCO_3$ (2 x 25 mL), and brine (25) mL), and dried over $MgSO_4$. The black solution was stirred with DARCO ® activated carbon for 15 minutes, and filtered through paper to give a light brown solution. Rotary evaporation of the solvents under reduced pressure gave 2.43 g of a viscous brown oil, which was shown by NMR spectra and thin-layer chromatography to contain a major proportion of α-(2-chloroethyl)-N,N-diethyl-1H-pyrrole-2-acetamide, (XII, X=Cl, Y=NEt₂), and minor proportions of the pyrrole-2,5- di(substituted acetamide) and unreacted N,N-diethyl-2-bromo-4-chloro-butanamide. Double Kugelrohr distillation (130°–135° C., 0.15 mm) afforded α-(2-chloroethyl)-N,N-diethyl-1H-pyrrole-2-acetamide as a white solid having NMR (CDCl₃) δ:

8.8–9.2 (1H, broad singlet)
6.6–6.8 (1H, multiplet)
6.0–6.2 (2H, multiplet)
4.24 (1H, triplet)
3.2–3.6 (6H, multiplet)
2.1–2.4 (2H, multiplet)
1.0–1.3 (6H, multiplet).

Example 5

Preparation of N,N-diethyl-2,3-dihydro-1H-pyrrolo[1,2-a]pyrrole-1-caboxamide. (Step 3)

A. Sodium hydride (Aldrich, 50% in mineral oil, 0.140 g, 2.91 mmol) was added to a 25 mL flask containing a stirrer bar, and washed with dry tetrahydrofuran (distilled over sodium, 4×5 mL). 10 mL tetrahydrofuran was added, followed by α-(2-chloroethyl)-N,N-diethyl-1H-pyrrole-2-acetamide (0.115 g, 0.47 mmol). The resulting mixture was stirred at room temperature for 3 hours, by which point tlc showed no starting material. Four drops of water were slowly added, producing vigorous gas evolution, and the mixture diluted with ether (50 mL) while being transferred to a separatory funnel. The solution was extracted with water (4×20 mL) and brine (20 mL), and dried over MgSO₄; and the solvents removed by vacuum rotary evaporation to afford 0.10 g of a light brown viscous oil, N,N-diethyl-2,3-dihydro-1H-pyrrolo[1,2-a]pyrrole-1-carboxamide (II, Y=NEt₂), having NMR (CDCl₃) δ:

6.58–6.61 (1H, multiplet)
6.17 (1H, triplet)
5.79 (1H, doublet)
2.8–4.3 (8H, multiplet)
2.4–2.8 (1H, multiplet)
1.26 (3H, triplet)
1.11 (3H, triplet).

Comparison of the NMR spectrum and R_f value with those of an authentic specimen of N,N-diethyl-2,3-dihydro1H-pyrrolo[1,2-a]pyrrole-1-carboxamide prepared from the corresponding acid showed that the materials were identical.

Example 6

Preparation of 2,3-dihydro-1H-pyrrolo[1,2-a]-pyrrole-1-carboxylic acid.

N,N-Diethyl-2,3-dihydro-1H-pyrrolo[1,2-a]pyrrole1-carboxamide is dissolved in ethylene glycol, and potassium hydroxide is added. The mixture is heated to 100° C. for 8 hours, cooled, and water added. The resulting mixture is acidified with concentrated HCl and extracted with methylene chloride. The organic layer is evaporated, and the residue sublimed at 55-60° C./0.1 mmHg to afford the title compound as a white solid.

Example 7

Preparation of methyl 2,3-dihydro-1H-pyrrolo[1,2-a]-pyrrole-1-carboxylate.

2,3-Dihydro-1H-pyrrolo[1,2-a]pyrrole-1-carboxylic acid is dissolved in methanol containing a small amount of concentrated hydrochloric acid. The resulting solution is heated to reflux, and then cooled. The title compound is isolated by rotary evaporation of the solvent under reduced pressure, and may be purified by chromatography on silica gel with hexane/ethyl acetate as eluent.

We claim:

1. A process for producing a compound of formula IX.

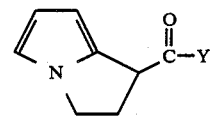

(IX)

in which Y is
OH;
O⁻M⁺, wherein M is an alkali metal; or
NRR', wherein R is lower alkyl and R' is lower alkyl or aryl, or NRR' is the residue of a saturated cyclic amine,
which comprises the reaction of a compound of formula XII,

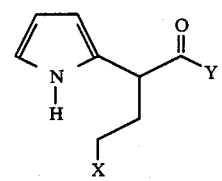

(XII)

in which
Y is as previously defined; and
X is halogen,
with a strong base in an aprotic polar solvent.

2. The process of claim 1 wherein the reaction temperature is between about 15° and 25° C.

3. The process of claim 1 wherein the reaction time is between about 10 minutes and 10 hours.

4. The process of claim 3 wherein the reaction time is between about 1 and 5 hours.

5. The process of claim 1 wherein Y is NRR'.

6. The process of claim 1 wherein the strong base is an alkali metal hydride.

7. The process of claim 1 wherein the aprotic polar solvent is tetrahydrofuran.

8. The process of claim 1 wherein Y is O⁻M⁺ or NRR', which further comprises the step of hydrolyzing the compound of formula (IX, Y=O⁻M⁺ or NRR') to afford a compound of formula (IX, Y=OH).

9. A process for producing a compound of formula XII.

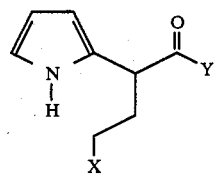

(XII)

in which
Y is OH,
O⁻M⁺, wherein M is an alkali metal, or

NRR', wherein R is lower alkyl and R' is lower alkyl or aryl, or NRR' is the residue of a saturated cyclic amine; and X is halogen, which comprises the reaction of a compound of formula X,

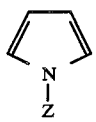 (X)

in which Z is Li, MgCl, or MgBr,
with a compound of formula XI,

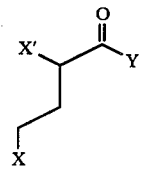 (XI)

in which
X and Y' are as previously defined; and X' is halogen.

10. The process of claim 9 wherein the reaction temperature is between about 0° and 60° C.

11. The process of claim 10 wherein the reaction temperature is between about 0° and 40° C.

12. The process of claim 9 wherein the reaction time is between about 30 minutes and 48 hours.

13. The process of claim 12 wherein the reaction time is between about 5 and 20 hours.

14. The process of claim 9 wherein X is Cl and X' is Br.

15. The process of claim 9 wherein Y is NRR'.

16. The process of claim 9 wherein Z is Li.

17. A compound of formula XII,

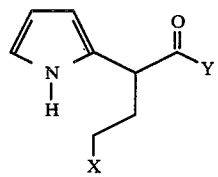 (XII)

in which
X is halogen; and
Y is OH;
$O-M+$, wherein M is an alkali metal; or NRR', wherein R is lower alkyl and R' is lower alkyl or aryl, or NRR' is the residue of a saturated cyclic amine.

18. The compound of claim 17 wherein X is chlorine.

19. The compound of claim 17 wherein Y is NRR'.

20. The compound of claim 18 wherein Y is NRR' and R and R' are each lower alkyl.

* * * * *